United States Patent [19]

Hogue-Angeletti et al.

[11] Patent Number: 5,514,775

[45] Date of Patent: May 7, 1996

[54] CHROMOGRANIN PEPTIDES

[75] Inventors: Ruth Hogue-Angeletti, New Rochelle; John Russell, Bronx, both of N.Y.

[73] Assignee: Albert Einstein College of Medicine of Yeshiva University, a Division of Yeshiva University, Bronx, N.Y.

[21] Appl. No.: 75,391

[22] Filed: Jun. 9, 1993

[51] Int. Cl.$^6$ .............................. C07K 5/00; C07K 7/00; C07K 17/00

[52] U.S. Cl. ............................................ 530/326; 530/324

[58] Field of Search ...................................... 530/324, 326

[56] References Cited

PUBLICATIONS

"The Chromogranin A and B: The First 25 Years and Future Perspectives", by Winkler et al., in *Neuroscience*, vol. 49, No. 3, pp. 497–528 (1992).

"Chromogranin A: Its Role In Endocrine Function and as an Endocrine and Neuroendocrine Tumor Marker", by Deftos, in *Endocrine Reviews*, vol. 12, No. 2, pp. 181–187 (1991).

"Bovine Parathyroid Glands Secrete a 26–kDa N–Terminal Fragment of Chromogranin–A which Inhibits Parathyroid Cell Secretion", by Drees et al., in *Endocrinology*, vol. 129, No. 6, pp. 3381–3387 (1991).

"A Chromogranin A–Derived Peptide Differentially Regulates the Secretion of Calcitonin Gene Products", by Deftos et al., in *Journal of Bone and Mineral Research*, vol. 5, No. 9, pp. 989–991 (1990).

"Autocrine Regulation of Parathyroid Secretion: Inhibition of Secretion by Chromogranin–A (Secretory Protein–I) and Potentiation of Secretion by Chromogranin–A and Pancreastatin Antibodies", by Fasciotto et al., in *Endocrinology*, vol. 127, No. 3, pp. 1329–1335 (1990).

"PTHrP Secretion is Stimulated by CT and Inhibited by CgA Peptides" by Deftos et al., in *Endocrinology*, vol. 125, No. 1, pp. 563–565 (1989).

"Pancreastatin, a Presumed Product of Chromogranin–A (Secretory Protein–I) Processing, Inhibits Secretion from Porcine Parathyroid Cells in Culture", by Fasciotto et al., in *Endocrinology*, vol. 125, No. 3, pp. 1617–1622 (1989).

"The Sequence of Porcine Chromogranin A Messenger RNA Demonstrates Chromogranin A Can Serve as the Precursor for the Biologically Active Hormone Pancreastatin", by Iacangelo et al., in *Endocrinology*, vol. 122, No. 5, pp. 2339–2341 (1988).

"The Primary Structure of Human Secretonin I (Chromogranin B): Comparison with Chromogranin A Reveals Homologous Terminal Domains and a Large Intervening Variable Region", by Benedum et al., in *The EMBO Journal*, vol. 6, No. 5, pp. 1203–1211 (1987).

"Pancreastatin, a Novel Pancreatic Peptide that Inhibits Insulin Secretion", by Tatemoto et al., in *Nature*, vol. 324, pp. 476–478 (Dec. 4, 1986).

"The Molecular Function of Adrenal Chromaffin Granules: Established Facts and Unresolved Topics", by Winkler et al., in *Neuroscience*, vol. 18, No. 2, pp. 261–290 (1986).

"Secretogranins I and II: Two Tyrosine–Sulfated Secretory Proteins Common to a Variety of Cells Secreting Peptides by the Regulated Pathway", by Rosa et al., in *Journal of Cell Biology*, vol. 101, pp. 1999–2011 (Nov., 1985).

*Primary Examiner*—Jill Warden
*Assistant Examiner*—Sheela J. Huff
*Attorney, Agent, or Firm*—Amster, Rothstein & Ebenstein

[57] ABSTRACT

This invention relates to the preparation and use of shortened synthetic chromogranin peptides capable of inhibiting parathyroid hormone secretion. The shortened synthetic chromogranin peptides of the invention are administered to treat hyperparathyroidism and to reverse bone resorption.

1 Claim, 5 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 41
        ( B ) TYPE: amino acid
        ( C ) STRANDEDNESS: single
        ( D ) TOPOLOGY: circular ( i i ) MOLECULE TYPE: DNA
        ( A ) DESCRIPTION:chromogranin B peptide ( i i i ) HYPOTHETICAL: No ( i v ) ANTI-SENSE: No ( v ) FRAGMENT TYPE: N-terminal fragment ( v i ) ORIGINAL SOURCE:
        ( A ) ORGANISM: bovine
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: Not Applicable ( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: chromogranin B
        ( B ) LOCATION: $CGB_{1-41}$
        ( C ) IDENTIFICATION METHOD:
        ( D ) OTHER INFORMATION:

( x ) PUBLICATION INFORMATION: None
        ( A ) AUTHORS:
        ( B ) TITLE:
        ( C ) JOURNAL:
        ( D ) VOLUME:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 1:

```
Met Pro Val Asp Asn Arg Asn His Asn Glu Gly Met Val Thr Arg Cys          16

Ile Ile Glu Val Leu Ser Asn Ala Leu Ser Lys Ser Ser Ala Pro Pro          32

Ile Thr Pro Glu Cys Arg Gln Val Leu                                      41
```

( 2 ) INFORMATION FOR SEQ ID NO: 2:

( i ) SEQUENCE CHARACTERISTICS:
        ( A ) LENGTH: 40
        ( B ) TYPE: amino acid
        ( C ) STRANDEDNESS: single
        ( D ) TOPOLOGY: circular ( i i ) MOLECULE TYPE: DNA
        ( A ) DESCRIPTION: chromogranin A peptide (i i i) HYPOTHETICAL: No (i v) ANTI-SENSE: No (v) FRAGMENT TYPE: N-terminal fragment (v i) ORIGINAL SOURCE:
    (A) ORGANISM: bovine
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE: Not Applicable (v i i i) POSITION IN GENOME:
    (A) CHROMOSOME/SEGMENT:
    (B) MAP POSITION:
    (C) UNITS:

(i x) FEATURE:
    (A) NAME/KEY: chromogranin A
    (B) LOCATION: $CGA_{1-40}$
    (C) IDENTIFICATION METHOD:
    (D) OTHER INFORMATION:

(x) PUBLICATION INFORMATION: Abstract
    (A) AUTHORS: Hogue-Angeletti et al
    (B) TITLE: Amino Terminal Chromogranin A Peptides
        Inhibit Secretion From Thyroid Cells
    (C) JOURNAL:
    (D) VOLUME:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO: 2:

| | | | | | | | | | | | | | | | | |
|---|---|---|---|---|---|---|---|---|---|---|---|---|---|---|---|---|
| Leu | Pro | Val | Asn | Ser | Pro | Met | Asn | Lys | Gly | Asp | Thr | Glu | Val | Met | Lys | 16 |
| Cys | Ile | Val | Glu | Val | Ile | Ser | Asp | Thr | Leu | Ser | Lys | Pro | Ser | Pro | Met | 32 |
| Pro | Val | Ser | Lys | Glu | Cys | Phe | Glu | | | | | | | | | 40 |

(2) INFORMATION FOR SEQ ID NO: 3:

(i) SEQUENCE CHARACTERISTICS:
        (A) LENGTH: 22
        (B) TYPE: amino acid
        (C) STRANDEDNESS: single
        (D) TOPOLOGY: circular (i i) MOLECULE TYPE: DNA
        (A) DESCRIPTION: chromogranin A peptide (i i i) HYPOTHETICAL: No (i v) ANTI-SENSE: No (v) FRAGMENT TYPE: N-terminal fragment (v i) ORIGINAL SOURCE:
        (A) ORGANISM: bovine
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE: Not Applicable (viii) POSITION IN GENOME:
         (A) CHROMOSOME/SEGMENT:
         (B) MAP POSITION:
         (C) UNITS:

(ix) FEATURE:
         (A) NAME/KEY: chromogranin A
         (B) LOCATION: $CGA_{17-38}$
         (C) IDENTIFICATION METHOD:
         (D) OTHER INFORMATION:

(x) PUBLICATION INFORMATION: Abstract
         (A) AUTHORS: Hogue-Angeletti et al
         (B) TITLE: Amino Terminal Chromogranin A Peptides
               Inhibit Secretion From Thyroid Cells
         (C) JOURNAL:
         (D) VOLUME:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 3:

Cys Ile Val Glu Val Ile Ser Asp Thr Leu Ser Lys Pro Ser Pro Met      16

Pro Val Ser Lys Glu Cys                                              22

CHROMOGRANIN PEPTIDES

STATEMENT OF GOVERNMENT INTEREST

This invention was made with government support under NIH Grant Numbers NS 22697 and DK 34288. As such, the government has certain rights in the invention.

FIELD OF THE INVENTION

This invention is directed to synthetic chromogranin peptides and the use of said peptides to treat hyperparathyroidism and reverse bone resorption. Specifically, the peptides of this invention are shortened synthetic chromogranin peptides capable of inhibiting parathyroid hormone secretion. These peptides are administered to treat hyperparathyroidism, parathyroid hyperplasia-associated renal failure and osteoporosis, and to reverse bone resorption and repair bone fracture.

BACKGROUND OF THE INVENTION

Chromogranin A (CGA) and chromogranin B (CGB) are large, acidic proteins found in the secretry granules of a wide variety of endocrine and neuroendocrine tissues including the parathyroid. It has been determined that chromogranin A is present in relatively high concentrations in the parathyroid (see Takatsuki et al., *J. Biol. Chem.*, Vol. 256, pp. 2342–2345 (1981) and Cohn et al., *Biochemistry*, Vol. 20, pp. 4135–4140 (1981)). In addition, it has been determined that chromogranin A is co-secreted with parathyroid hormone in response to changes in extracellular calcium (see Cohn et al., *Endocrinology*, Vol. 110, pp. 625–630 (1982)).

Although little is known about the function of chromogranins, there is a growing body of evidence that suggests that chromogranins may be precursors for a number of biologically active peptides. Chromogranin A has been shown to inhibit parathyroid hormone secretion in primary cultures of parathyroid cells (see Fasciotto et al., *Endocrinology*, Vol. 127, pp. 1329–1335 (1990)). In addition, it has been indicated that the amino terminal region of the protein is responsible for this activity (see Drees et al., *Endocrinology*, Vol. 129, pp. 3381–3387 (1991)). Further, it has been reported that amino terminal peptide $CGA_{1-40}$ stimulates secretion of the hormone CGRP and inhibits secretion of calcitonin (see Deftos et al., *J. Bone Min. Res.*, Vol. 5, pp. 989–991 (1990)). However, to date, no chromogranin B peptides have been reported, and no synthetic chromogranin A or chromogranin B peptides have been developed which are capable of inhibiting parathyroid hormone secretion. In addition, no shortened synthetic chromogranin peptides having similar properties to full-length chromogranin peptides (i.e., inhibiting parathyroid hormone secretion) have been developed.

The inventors have not only prepared synthetic chromogranin A peptides which are capable of inhibiting parathyroid hormone secretion, but have synthesized very short chromogranin A peptides which correspond to part of the amino terminal sequence of naturally-occurring chromogranin A, which peptides are capable of inhibiting parathyroid hormone secretion. In addition, the inventors have also developed a shortened synthetic chromogranin B peptide capable of inhibiting parathyroid hormone secretion.

It is therefore an object of this invention to provide shortened synthetic chromogranin peptides capable of inhibiting parathyroid hormone secretion.

It is a further object of this invention to provide a method of treating hyperparathyroidism and parathyroid hyperplasia-associated renal failure utilizing shortened synthetic chromogranin peptides capable of inhibiting parathyroid hormone secretion.

It is a still further object of this invention to provide a method of preventing or reversing bone resorption, thereby repairing bone fracture utilizing shortened synthetic chromogranin peptides capable of inhibiting parathyroid hormone secretion.

It is another object of this invention to provide a method of treating osteoporosis utilizing shortened synthetic chromogranin peptides capable of inhibiting parathyroid hormone secretion.

SUMMARY OF THE INVENTION

This invention is directed to shortened synthetic chromogranin peptides capable of inhibiting low calcium-induced parathyroid hormone secretion. The peptides of this invention have amino acid sequences which correspond to at least part of the amino terminal sequence of natural chromogranin found in endothelial cells, and comprise or contain therein an amino acid sequence having circular topology (circular structure) formed by covalent bond. The peptides of this invention are administered to treat hyperparathyroidism, parathyroid hyperplasia-associated renal failure, and osteoporosis, and may also be administered to reverse bone resorption and repair bone fracture.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 2A represents an analysis of inhibition of parathyroid hormone secretion by $CGA_{1-76}$ at 0.5 and 1.75 mM CA++; FIG. 2B represents an analysis of inhibition of parathyroid hormone secretion by $CGB_{1-41}$, $CGA_{1-40}$ and $CGA_{17-38}$ (disulfide loop only);

DETAILED DESCRIPTION OF THE INVENTION

Figure 1:
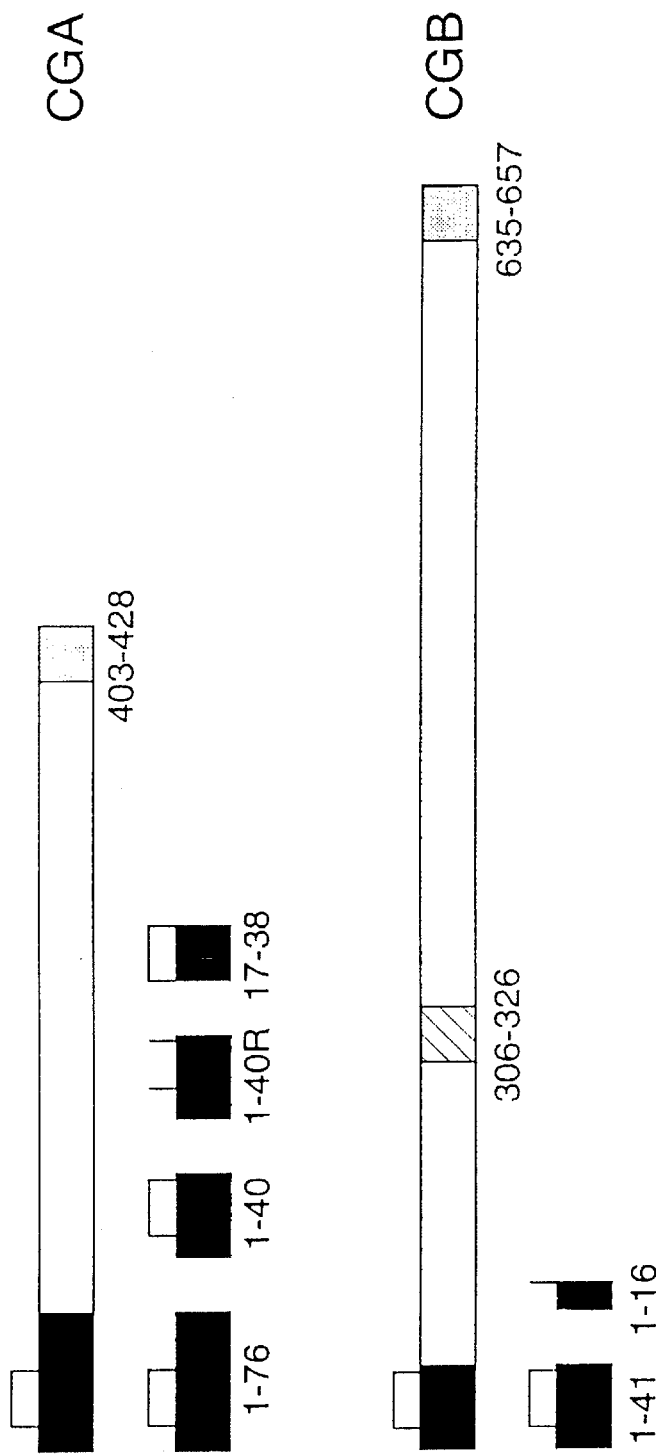
FIG. 1 represents synthetic CGA and CGB peptides tested for biological activity using dispersed bovine parathyroid cells.

This invention is directed to shortened synthetic chromogranin peptides capable of inhibiting parathyroid hormone secretion and the use of these peptides to treat hyperparathyroidism, parathyroid hyperplasia-associated renal failure and for preventing or reversing bone resorption, thereby preventing or treating osteoporosis and repairing bone fracture.

Utilizing tBoc chemical strategy or Fmoc chemical strategy, three shortened synthetic chromogranin peptides have been produced by the inventors. Peptides were synthesized by solid phase peptide synthesis using either tBoc or Fmoc protection strategies, similar to those routinely used on automated instruments such as the Applied Biosystems 430A instrument or similar to those outlined in "Synthetic Peptides: A User's Guide", Gregory A. Grant, editor, W. H. Freeman & Co. publisher, New York (1992). After cleavage from the resin by HF (for tBoc strategy) or trifluoroacetic acid (Fmoc strategy), the peptides were extracted with acetic acid solutions, lyophilized and then purified by reversed phase high performance liquid chromatography on a C-18 or C-8 bonded phase column. The disulfide bond was formed by simple air oxidation. The structures of the peptides were verified by mass spectrometry and amino acid composition analysis.

One of the synthesized peptides is a chromogranin B peptide, which has an amino acid sequence that corresponds to the amino terminal sequence $CGB_{1-41}$. It has the following amino acid sequence:

SEQ ID NO. 1: Met Pro Val Asp Asn Arg Asn His Asn Glu Gly Met Val Thr Arg Cys Ile Ile Glu Val Leu Ser Asn Ala Leu Ser Lys Ser Ser Ala Pro Pro Ile Thr Pro Glu Cys Arg Gln Val Leu.

Two of the synthesized peptides are chromogranin A peptides. One of these chromogranin A peptides has an amino acid sequence which corresponds to natural $CGA_{1-40}$, and has the following amino acid sequence:

SEQ ID NO. 2: Leu Pro Val Asn Ser Pro Met Asn Lys Gly Asp Thr Glu Val Met Lys Cys Ile Val Glu Val Ile Ser Asp Thr Leu Ser Lys Pro Ser Pro Met Pro Val Ser Lys Glu Cys Phe Glu.

The second chromogranin A peptide corresponds to natural $CGA_{17-38}$, is in loop form, and has the following amino acid sequence:

SEQ ID NO. 3: Cys Ile Val Glu Val Ile Ser Asp Thr Leu Ser Lys Pro Ser Pro Met Pro Val Ser Lys Glu Cys.

The shortened synthetic chromogranin peptides of the invention are capable of inhibiting low calcium-induced parathyroid hormone secretion. These shortened synthetic chromogranin peptides have amino acid sequences substantially similar to at least part of the amino terminal sequence of natural chromogranin found in endocrine cells. In addition, the peptides of the invention contain or comprise circular amino acid sequence structures which are formed by covalent bonds, such as disulfide bonds. The preferred shortened synthetic chromogranin peptides of this invention have between 15 and 45 amino acid residues.

The shortened synthetic chromogranin peptides of this invention can be administered in any manner, including orally, intraveneously, subcutaneously or intraperitoneally, to inhibit low calcium-induced parathyroid hormone secretion. Because the peptides of this invention inhibit parathyroid hormone secretion, they are effective in treating hyperparathyroidism and parathyroid hyperplasia-associated renal failure. In addition, the peptides of this invention are effective in reversing bone resorption, and therefore can be administered to prevent or treat osteoporosis and to repair bone fracture.

In order to show that the shortened synthetic chromogranin peptides of the invention are capable of inhibiting parathyroid hormone secretion, synthesized peptides were added to culture medium and put into contact with bovine parathyroid cells. In order to prepare bovine parathyroid cells, bovine parathyroid glands were obtained by neck dissection of bovines, trimmed of excess fat and minced. Tissue fragments were enzymatically digested according to the method described by Brown et al., *Endocrinology*, Vol. 90, pp. 1582–1588 (1976) for 3 hours in sterile BME containing 2 mg/ml collagenase, 0.75 mM magnesium and 1 mM calcium. After digestion, the cells were filtered through 200 M sterile gauze, rinsed 4 times in sterile BME and plated in 24-well Falcon dishes. Before incubation, cell number and viability were determined by direct cell count with a hemocytometer and trypan blue dye exclusion, respectively.

Prior to initiation of the experimental procedures, the parathyroid cells were allowed to attach by overnight incubation in BME with 10% fetal bovine serum, 1% penicillin-streptomycin, 1 mM magnesium and 1 mM calcium. At the beginning of each experiment, old medium was removed and the cells were washed twice and replenished with fresh medium containing 2% fetal bovine serum, 1 mM magnesium, the desired level of calcium and the appropriate peptide to be tested. Each test was conducted in quadruplicate. After 3 hours of incubation, the medium was removed for assay of parathyroid hormone and the cells were harvested and lysed for protein determination by the method described by Petersen, *Anal. Biochem.*, Vol. 83, pp. 346–356 (1977), with the modification that the Lowry reagents were modified to obtain a stable alkaline-copper reagent, which facilitated the simplicity of the assay.

FIG. 1 represents the synthetic chromogranin A (CGA) and chromogranin B (CGB) peptides that were tested for biological activity using dispersed bovine parathyroid cells. The amino terminal peptides are indicated by solid black, with the disulfide loop (17–38 in CGA and 16–37 in CGB) being indicated by the closed rectangle. The structure 1–40R represents $CGA_{1-40}$ in which the disulfide bond has been disrupted by reduction and alkylation of both cystine residues. All of the amino terminal peptides, with the exception of $CGB_{1-16}$ and reduced and alkylated $CGA_{1-40}$, contain the disulfide loop structure consisting of 22 amino acids.

Parathyroid hormone secretion was measured by radioimmunoassay. Parathyroid cells were cultured for 24 hours prior to the beginning of the experiment. At that time, cells were washed twice with culture medium and replaced with fresh culture medium containing either 0.5 or 1.75 mM $CA^{++}$. In addition, two groups of cells in low calcium received either $10^{-8}$ or $10^{-7}$ M $CGA_{1-76}$. The statistical analysis represents the results from 8 replicates for each experimental condition where $*=p<0.02$ and $**=p<0.001$. At 0.05 mM $CA^{++}$, exposure of parathyroid cells to $CGA_{1-76}$ for 3 hours resulted in a dose dependent decrease in parathyroid hormone secretion. At concentrations of $10^{-8}$ and $10^{-7}$ parathyroid hormone secretion was inhibited by 30% and 50%, respectively, the latter being comparable to the inhibitory effect of 1.75 mM $CA^{++}$.

Figure 2:
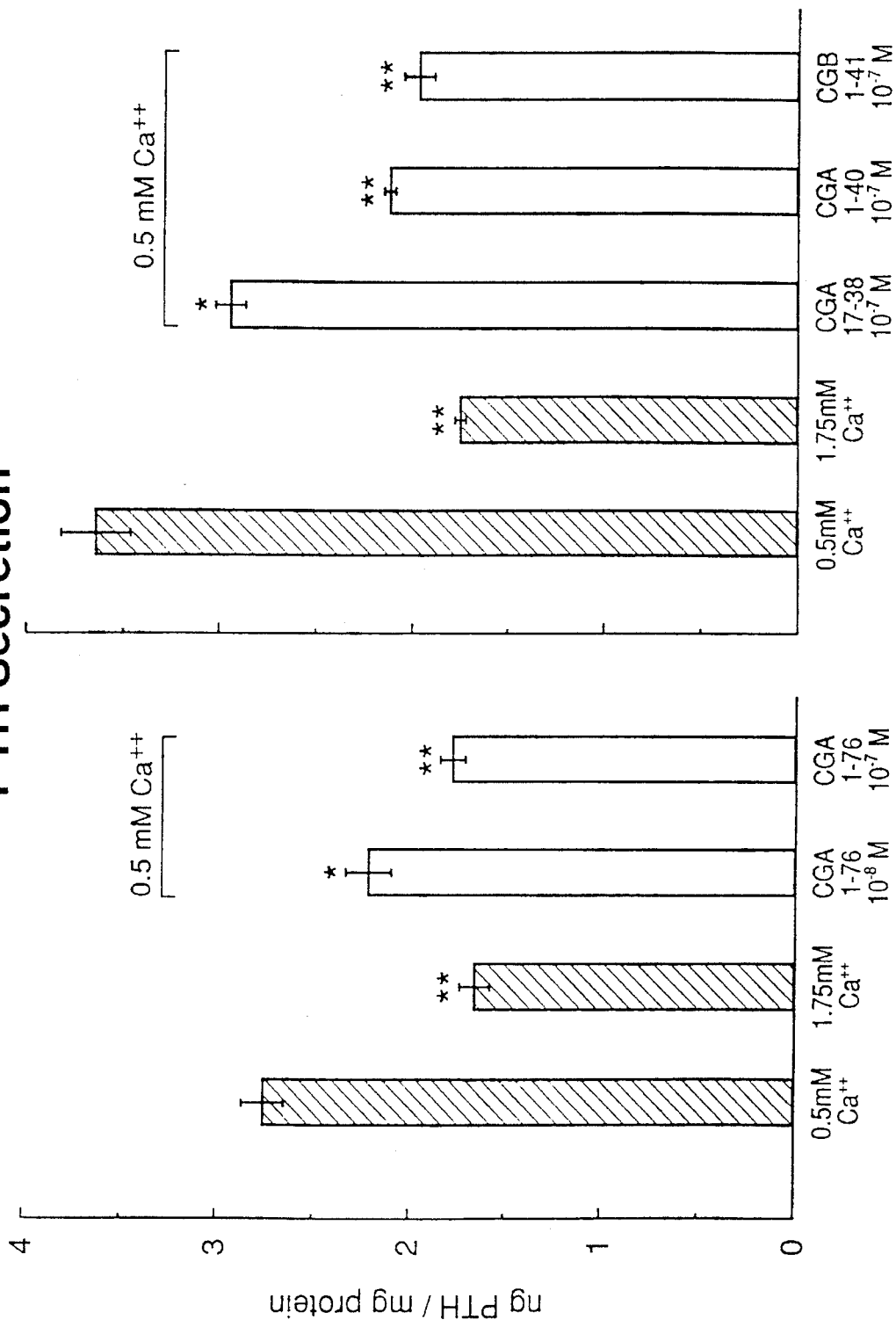
FIG. 2A and FIG. 2B.

Next, bovine parathyroid cells were cultured, washed and replenished with fresh medium as described in FIG. 2A. However, in this experiment, three groups of cells in low calcium received synthetic fragments $CGB_{1-41}$, $CGA_{1-40}$ and $CGA_{17-38}$ (disulfide loop only). As shown in FIG. 2B, $CGA_{1-40}$ and $CGB_{1-41}$, at concentrations of $10^{-7}$ M, inhibited parathyroid hormone secretion to the same extent as 1.75 mM $CA^{++}$. At the same concentration $CGA_{17-38}$, which contains only the disulfide loop structure, also was able to inhibit parathyroid secretion, but to a lesser degree (25%). The effects were completely reversible, since parathyroid hormone secretion returned to control levels once the amino terminal peptides were no longer present. Table I, below, represents the parathyroid hormone secretion of $CGA_{1-40}$ at 1 hour, 2.5 hours and 5 hours. Table II, below, represents parathyroid hormone secretion of bovine parathyroid cells in the presence of chromogranin peptides $CGA_{1-40}$, $CGB_{1-41}$ and $CGA_{17-38}$ (loop). Statistical analysis represents the results from 6 replicate plates from each experimental condition where *=p<0.02 and **=p<0.001.

TABLE I

Parathyroid Hormone Secretion in ng/hr/$10^6$ cells

|  | I<br>0.5 mM $Ca^{++}$ | II<br>1.5 mM $Ca^{++}$ | III<br>0.5 mM $Ca^{++}$ + $CGA_{1-40}$ |
| --- | --- | --- | --- |
| 1 hour | 4.2 ± 0.17 | 2.7 ± 0.16 | 2.6 ± 0.10 |
| 2.5 hours | 3.7 ± 0.22 | 2.5 ± 0.20 | 3.1 ± 0.20 |
| 5 hours | 4.4 ± 0.18 | 2.8 ± 0.15 | 3.9 ± 0.09 |
| 1 hour | I vs II p <0.001; | I vs III p <0.001; | II vs III NS |
| 2.5 hours | I vs II p <0.02; | I vs III p <0.05; | II vs III NS |
| 5 hours | I vs II p <0.001; | I vs III p <0.05; | II vs III NS p <0.001 |

TABLE II

Parathyroid Hormone (PTH) Secretion in the presence of chromogranin peptides

| Sample | [$CA^{2+}$] | Picograms PTH |
| --- | --- | --- |
| 1) low calcixun | 0.5 mM | 364 ± 17.8 |
| 2) high calcium | 1.75 mM | 175 ± 3.3 |
| 3) $CGA_{1-40}$ | 0.5 mM | 212 ± 3.0 |
| 4) $CGB_{1-41}$ | 0.5 mM | 197 ± 7.1 |
| 5) $CGA_{17-38}$ (loop) | 0.5 mM | 294 ± 8.4 |

1 vs 2, p <0.001
1 vs 3, p <0.001
2 vs 3, p <0.001
1 vs 4, p <0.001
2 vs 4, p <0.05
1 vs 5, p <0.02

Figure 3:
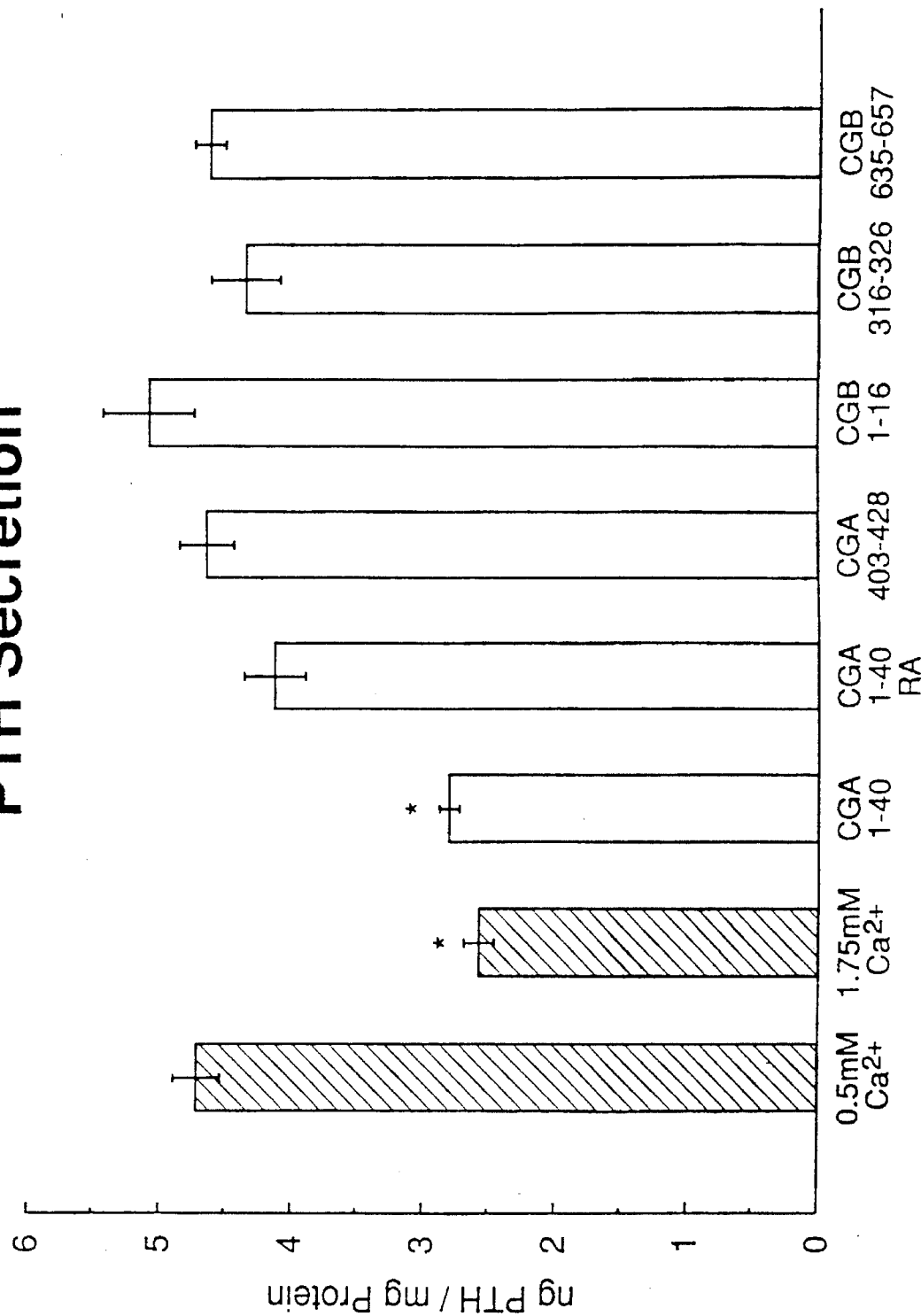
FIG. 3 represents a comparison of the effects of modified amino terminal peptides and peptides from regions other than the amino termini of CGA or CGB on parathyroid hormone secretion with that of $CGA_{1-40}$.

In contrast to the amino terminal peptides, peptides derived from other regions of CGA and CGB, which included $CGA_{403-428}$, $CGB_{1-16}$, $CGB_{316-326}$ and $CGB_{635-657}$, had no significant effect on parathyroid hormone secretion. FIG. 3 represents a comparison of the effects of modified amino terminal peptides or peptides from regions other than the amino termini of CGA or CGB on parathyroid hormone secretion with that of $CGA_{1-40}$. Each peptide was incubated for 3 hours at a concentration of $10^{-7}$ M in the presence of low calcium. An asterisk indicates a significance of p<0.02. Where there is no asterisk, this indicates that no significant differences were detected. In addition, the inhibitory activity of $CGA_{1-40}$ was abolished following reduction and alkylation.

Figure 4:
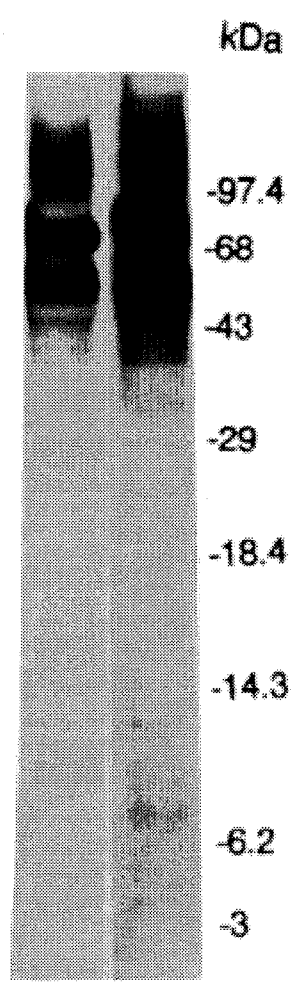
FIG. 4 represents an autoradiogram of $^{35}$S-labelled CGA peptides immunoprecipitated by anti-$CGA_{1-76}$ from medium of cultured bovine parathyroid cells stimulated to secrete by low Ca++.

In order to determine whether amino terminal peptides of CGA are processed and secreted by parathyroid cells, pulse chase experiments using $^{35}$S-methionine were performed. Labelled amino terminal CGA peptides were identified by immunoprecipitation with antisera specific for $CGA_{1-76}$ followed by SDS polyacrylamide gel electrophoresis. FIG. 4 represents an autoradiogram of $^{35}$S-labelled CGA polypeptides immunoprecipitated by anti-$CGA_{1-76}$ from medium of cultured bovine parathyroid cells stimulated to secrete by low $Ca^{++}$. Cells were pulsed with labelled methionine for 30 minutes, washed and then chased for 2 hours into medium with low $Ca^{++}$. After immunoprecipitation with anti-$CGA_{1-76}$, the labelled polypeptides were separated on 10–20% SDS-PAGE. The left lane shows a 3 day exposure. The right lane shows a 6 day exposure. The right lane shows several low molecular weight CGA amino terminal peptides, including one at 8 kDa, which co-migrated with synthetic $CGA_{1-76}$. The smaller peptides were less well labelled because of the lower number of methionine residues present. This is only a qualitative assessment, since methionine content in $CGA_{1-76}$ is considerably less than that of the intact protein and, therefore, it is not possible to quantitate relative amounts from this type of analysis.

Since the biological activity of the amino terminal peptides suggested that they may interact with some protein on the cells' surface, binding studies were performed in which $^{125}$I labelled amino terminal CGA or CGB peptides were incubated with cultured parathyroid cells and then cross-linked to bound proteins by the addition of dimethypinelimidate. In order to perform binding and cross-linking of $CGA_{1-40}$ and $CGB_{1-41}$ to parathyroid cells, cells were incubated with the radioiodinated peptides in Krebs-Ringer solution at 4° C. The cells were washed 3 times with Krebs-Ringer solution at 4° C. and then 1 mM dimethypinelimidate was added to the cells for 20 minutes at room temperature. The reaction was quenched by adding 10 mM ammonium acetate and the cells were dissolved in 1% SDS for separation by SDS-PAGE.

Figure 5:
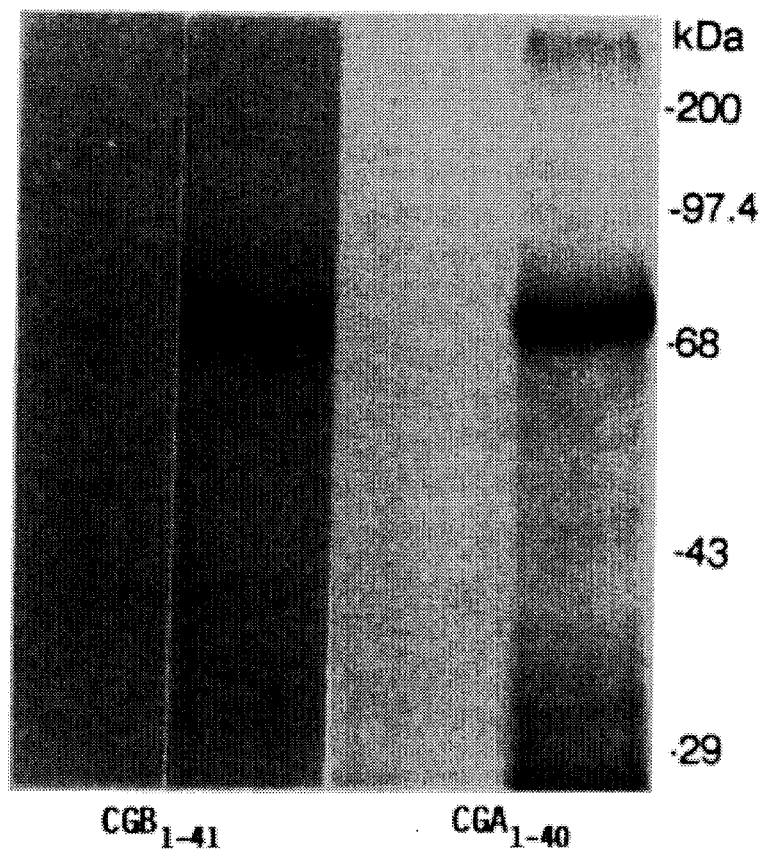
FIG. 5 represents binding and crosslinking of $CGA_{1-40}$ and $CGB_{1-41}$ to parathyroid cells by SDS-PAGE.

The left side of FIG. 5 shows the results of the binding and cross-linking performed in the presence of a large excess of cold peptides. The right side of FIG. 5 shows the results with radioiodinated peptide alone. With either $CGA_{1-40}$ or $CGB_{1-41}$, a single discreet band with an apparent molecular weight of 75 kDa was observed. As seen in the two adjacent lines, competition with excess cold peptide completely abolished the band. In addition, cold $CGA_{1-40}$ successfully competed with labelled $CGB_{1-41}$ and vice versa. Hence, the binding and cross-reactivity of $CGB_{1-41}$ and $CGA_{1-40}$ have been determined.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A synthetic chromogranin A peptide having the amino acid sequence Cys Ile Val Glu Val Ile Ser Asp Thr Leu Ser Lys Pro Ser Pro Met Pro Val Ser Lys Glu Cys (SEQ ID NO:3).

* * * * *